(12) United States Patent
Holder et al.

(10) Patent No.: US 7,412,904 B2
(45) Date of Patent: Aug. 19, 2008

(54) ISOKINETIC TESTING APPARATUS AND SYSTEM

(76) Inventors: Thomas L. Holder, 225 Brandywine Ave., Downingtown, PA (US) 19335; Donald R. Russell, 2798 Waverly Rd., Pawleys Island, SC (US) 29585

( * ) Notice: Subject to any disclaimer, the term of this patent is extended or adjusted under 35 U.S.C. 154(b) by 555 days.

(21) Appl. No.: 11/098,521

(22) Filed: Apr. 5, 2005

(65) Prior Publication Data

US 2006/0224087 A1   Oct. 5, 2006

(51) Int. Cl.
   *G01F 1/34* (2006.01)
(52) U.S. Cl. .................................................. 73/861.42
(58) Field of Classification Search ............ 73/379.01, 73/379.02, 379.03, 379.06; 600/595; 702/152
   See application file for complete search history.

(56) References Cited

U.S. PATENT DOCUMENTS

| | | | |
|---|---|---|---|
| 3,465,592 A | 9/1969 | Perrine | |
| 4,565,368 A | 1/1986 | Boettcher | |
| 4,691,694 A | 9/1987 | Boyd et al. | |
| 4,725,055 A | 2/1988 | Skowronski | |
| 4,772,015 A | 9/1988 | Carlson et al. | |
| 4,776,587 A | 10/1988 | Carlson et al. | |
| 4,802,462 A | 2/1989 | Reiss et al. | |
| 4,889,108 A | 12/1989 | Bond et al. | |
| 4,934,694 A | 6/1990 | McIntosh | |
| 4,984,568 A | 1/1991 | Persaud | |
| 5,015,926 A | 5/1991 | Casler | |
| 5,020,795 A | 6/1991 | Airy et al. | |
| 5,054,774 A | 10/1991 | Belsito | |
| 5,078,152 A | 1/1992 | Bond et al. | |
| 5,080,350 A | 1/1992 | Schofield et al. | |
| 5,179,939 A | 1/1993 | Donovan et al. | |
| 5,403,251 A | 4/1995 | Belsito et al. | |
| 5,417,643 A | 5/1995 | Taylor | |
| 5,529,552 A | 6/1996 | Biedermann et al. | |
| 5,558,624 A | 9/1996 | Hepburn et al. | |
| 5,618,250 A | 4/1997 | Butz | |
| 5,722,937 A | 3/1998 | Smith | |
| 5,791,351 A * | 8/1998 | Curchod | ................... 600/595 |
| 5,843,004 A | 12/1998 | Presl et al. | |
| 6,561,990 B1 | 5/2003 | Gilliam et al. | |
| 6,672,157 B2 * | 1/2004 | MacFarlane et al. | ..... 73/379.01 |
| 6,695,795 B2 | 2/2004 | Knoll | |

* cited by examiner

*Primary Examiner*—Jewel V Thompson
(74) *Attorney, Agent, or Firm*—Dennison, Schultz & MacDonald

(57) ABSTRACT

An isokinetic testing machine is disclosed having a support frame, a sub-assembly disposed on the support frame, a power source operably disposed within the sub-assembly, a first main arm having a proximal apex end and a distal end, the first main arm distal end is pivotally attached to the power source, a first torque arm pivotally and releasably attached to the first main arm proximal apex end, a user support area disposed on the support frame proximate to the first torque arm proximal end, a first load cell disposed within the first torque arm for measuring the torque when the first torque arm pivots, and wherein the first main arm and the torque arm can pivot and are configured to a desired position for isokinetic testing of the knees, the shoulders, and the back of the user.

27 Claims, 5 Drawing Sheets

ISOKINETIC TESTING APPARATUS AND SYSTEM

TECHNICAL FIELD

The present invention is directed generally toward an isokinetic testing apparatus and system and, more particularly, to a compact isokinetic testing apparatus and method for conducting strength tests of the knees, the shoulders, and the back in a single station.

BACKGROUND OF THE INVENTION

Isokinetic testing machines have been used to measure the strength of a person in order to determine whether that person has the suitable physical strength for a particular job or task.

Broadly, it has been customary for the person or individual to go to a clinic or isokinetic testing center. Generally, such tests involve measuring the strength of the knees, the shoulders, and the back of the person or client at various isokinetic stations each designed to perform the isokinetic testing machine specifically for the back, the shoulders, and the knees.

As a result, the use of these prior art isokinetic apparatus resulted in a time consuming, inconvenient, costly, and cumbersome procedure for the users and employers.

A further drawback of the prior art isokinetic testing machines is that they are relatively large and require a substantial space because they require multiple setups and stations for testing of the knees, the shoulders, and the back. Moreover, because the prior art isokinetic testing machines require multiple stations for the testing of the various joints, such tests become more time consuming and costly to the employers. For example, if a company or an employer wants to test a large number of employees at a specific on-site location, transporting and setting up prior art isokinetic testing machines can be very costly and time consuming.

It is therefore a primary object of the present invention to provide an isokinetic testing apparatus which can perform the isokinetic testing of a client's knees, shoulders, and the back in a single station in an efficient manner.

It is another object of the present invention to provide an isokinetic testing apparatus that is more compact and easily transportable.

It is yet another object of the present invention to provide an isokinetic testing apparatus that includes motorized arms, backrest, and seats to ease the physical demands of setting up and operating the apparatus.

It is a further object of the present invention to provide an isokinetic testing apparatus that can be easily and accurately configured and reconfigured for subsequent testing of a specific client or user.

SUMMARY OF THE INVENTION

An isokinetic testing machine is disclosed having a support frame, a sub-assembly disposed on the support frame, a power source operably disposed within the sub-assembly, a first main arm having a proximal apex end and a distal end, the first main arm distal end is pivotally attached to the power source, a first torque arm pivotally and releasably attached to the first main arm proximal apex end, a user support area disposed on the support frame proximate to the first torque arm proximal end, a first load cell disposed within the first torque arm for measuring the torque when the first torque arm pivots, and wherein the first main arm and the torque arm can pivot and are configured to a desired position for isokinetic testing of the knees, the shoulders, and the back of the user.

The invention also contemplates a method for isokinetic testing of an individual's knees, shoulders and back at a single station. The method includes the steps of providing an apparatus where the isokinetic testing of an individual's knees, shoulders and back at a single station and configuring the apparatus for isokinetic testing of the individual's knees, stabilizing the individual with respect to the apparatus and isokinetic testing of the individual's knees. The method also includes the steps of configuring the apparatus for isokinetic testing of the individual's shoulders, stabilizing the individual with respect to the apparatus and isokinetic testing of the individual's shoulders. Further, the method includes the steps of configuring the apparatus for isokinetic testing of the individual's back, stabilizing the individual with respect to the apparatus protecting the back, and isokinetic testing of the individual's back.

BRIEF DESCRIPTION OF DRAWINGS

These and other objects of the present invention will be appreciated and understood by those skilled in the art from the detailed description of the preferred embodiments of the invention and the following drawings of which.

DETAILED DESCRIPTION OF THE INVENTION

Figure 1:
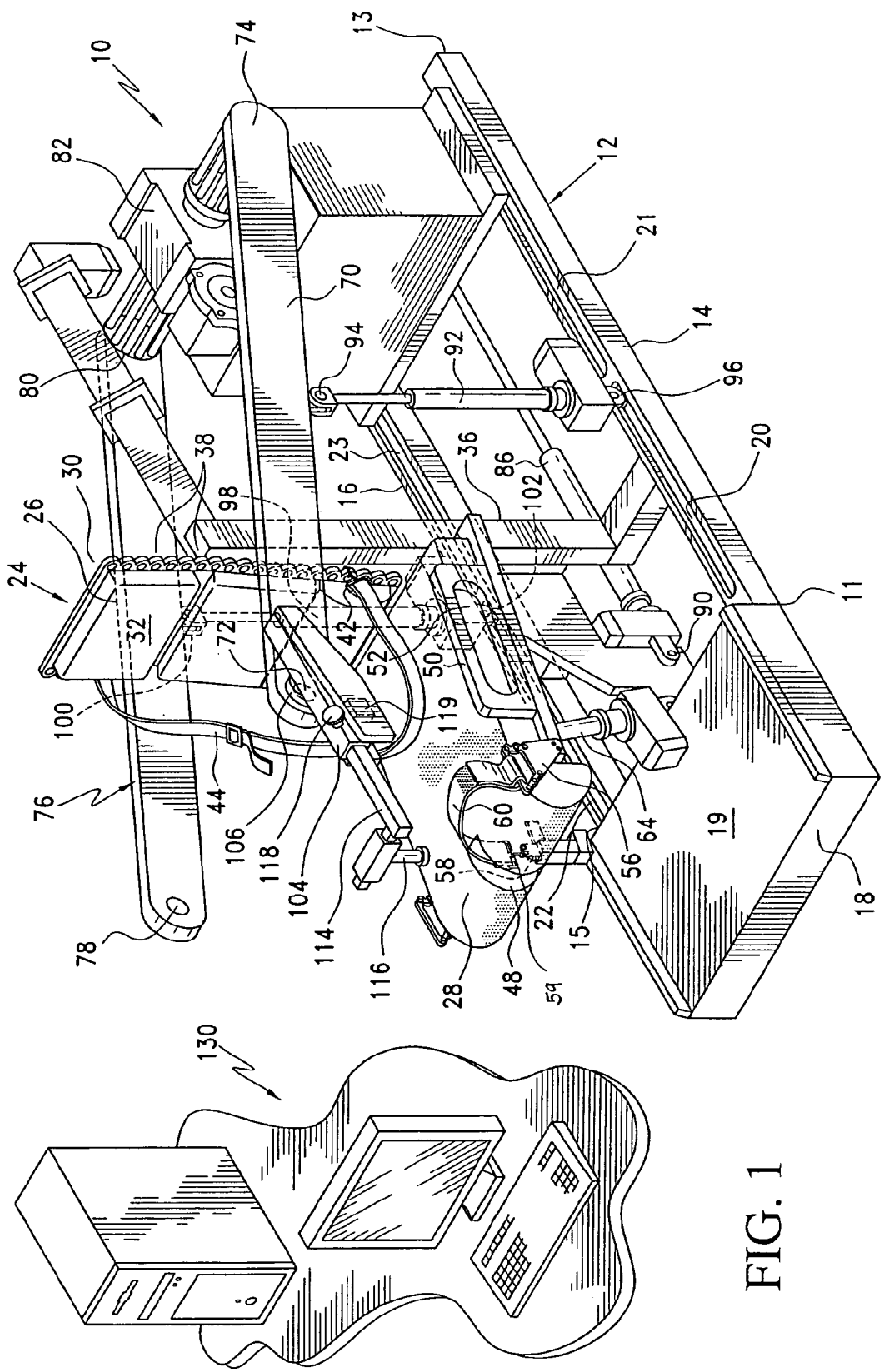
FIG. 1 is an isometric view of an isokinetic testing apparatus according to a first representative embodiment configured for testing of the left shoulder.
Figure 2:
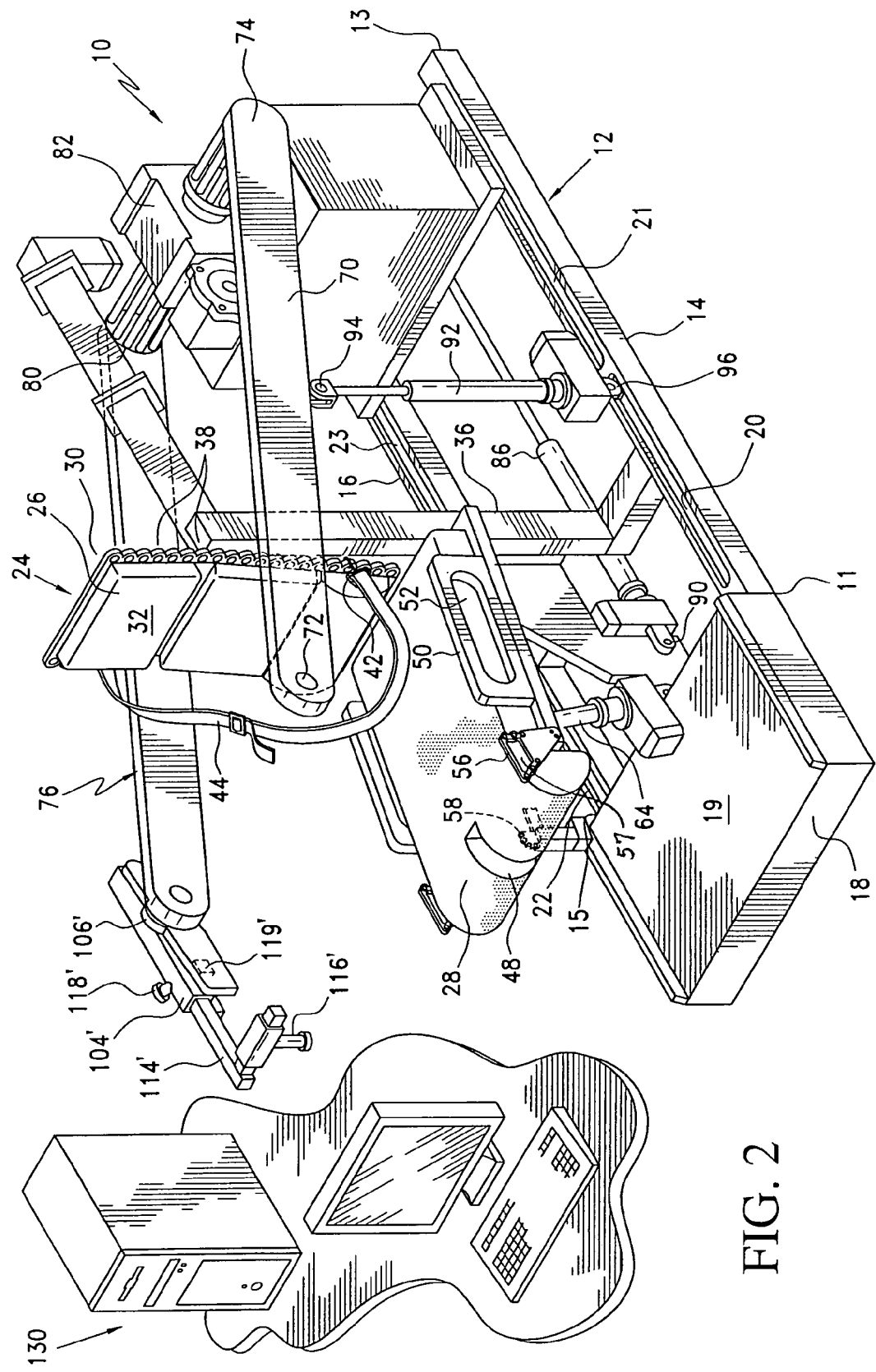
FIG. 2 is an isometric view of the isokinetic testing apparatus according to a first representative embodiment configured for testing of the right shoulder.
Figure 3:
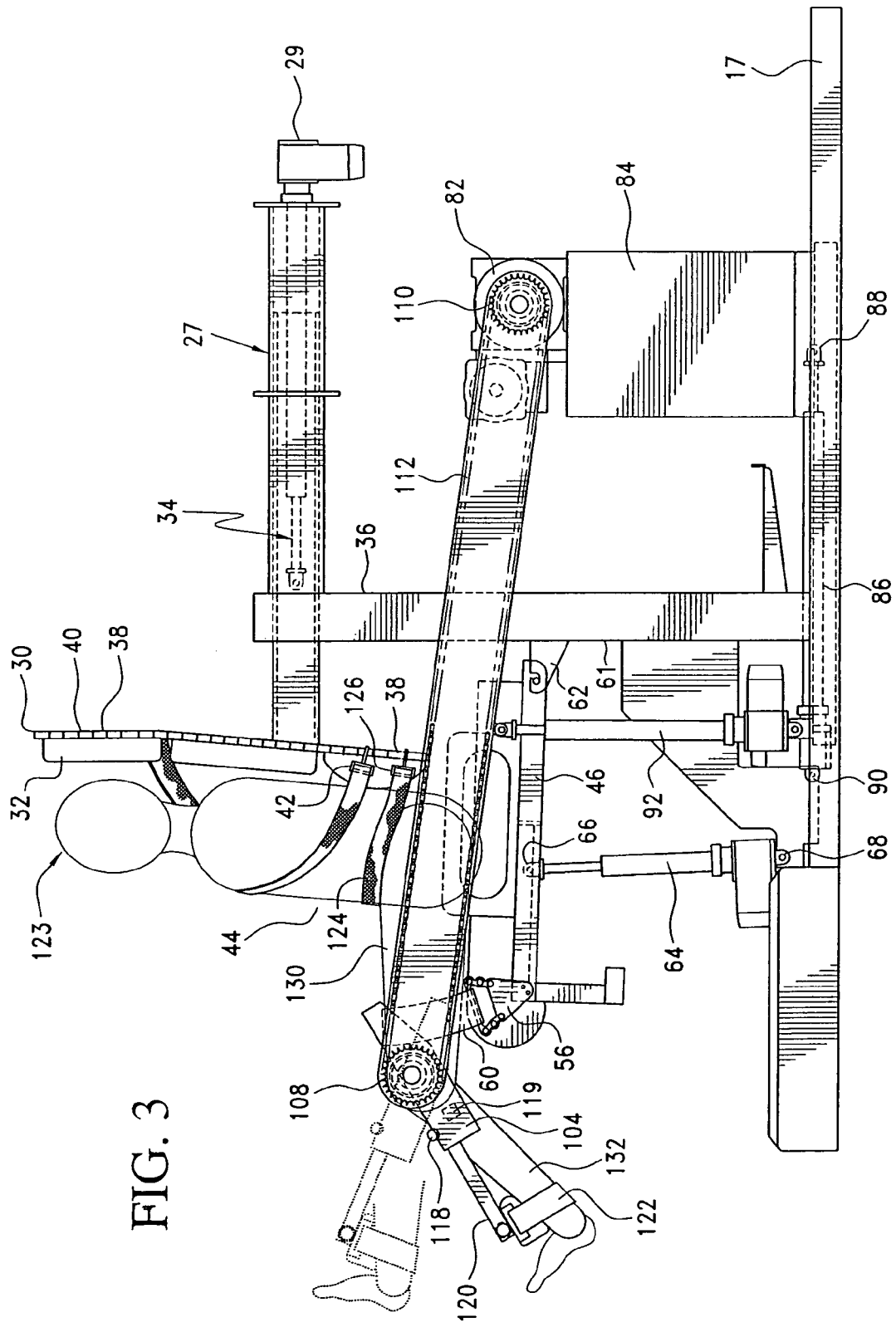
FIG. 3 is a side elevational view of the isokinetic testing apparatus according to a first representative embodiment being used by a client for testing of the left knee.

For the purpose of promoting and understanding of the principles of the invention, reference will now be made to the embodiments illustrated in the drawings. Referring now to the drawings, and more specifically FIGS. 1 through 3, wherein the showings are for the purpose of illustrating the preferred embodiment of the invention only and not for the purpose of limiting the same, an isokinetic testing apparatus 10 is illustrated having a support frame 12 preferably made from steel or other suitable material, comprising a first side or rail 14 and a second side or rail 16 for supporting the isokinetic testing apparatus on a support surface or floor. The first rail 14 includes a first end 11 and a second end 13, and the second rail 16 also includes a first end 15 and a second end 17.

A substantially rectangular-shaped support platform 18 is attached to or, in the alternative, may be integral with, the first end 11 of the first rail 14 and the first end 15 of the second rail 16. The support platform 18 includes an upper surface 19 wherein, as will be explained in greater detail, a user may stand thereon during the testing of the user's back.

The first rail 14 includes a first elongate slot or channel-type opening 20 extending on an upper section thereof, and a second elongate slot or channel-type opening 21 extending on an upper section thereof and separated from the first elongate slot 20 by a barrier. Similarly, the second rail 16 includes a first elongate slot or channel-type opening 22 extending on an upper section thereof, and a second elongate slot or channel-type opening 23 extending on an upper section thereof and separated from the first elongate slot 22 by a barrier.

The isokinetic testing apparatus 10 further includes an adjustable seat 24 having a vertical back portion 26 and an adjustable horizontal portion 28. The vertical back portion 26 includes a main plate 30 having a plurality of cushions 32 disposed on a front surface thereof. The main plate 30 is attached to a horizontally and telescopically movable first electric actuator arm 34 on a back surface thereof, wherein the first electric actuator arm 34 is slidably supported within a housing 27 which is further supported by a vertical post 36 attached to the first and the second rails 14, 16, of the support frame 12. The first electric actuator arm 34 is powered by a first actuator 29 operably disposed at one of the housing 27. The vertical back portion 26 further comprises a plurality of holes or apertures 38 disposed along a peripheral side 40 of the main plate 30, wherein each hole 38 is dimensioned and configured to receive a snap hook 42 of an adjustable first seat belt 44.

The adjustable horizontal portion 28 includes a frame 46 having a cushion 48 on an upper surface thereof, and a pair of handles 50 attached to each side of the frame 46. Each handle includes a cut-out section 52 for allowing the user to grab therethrough during a test. A second bracket 56 is attached to the front and side end of the frame 46 of the horizontal portion 28 at one end for receiving a second adjustable seatbelt 60 through an elongated slot 57 at an opposing second end thereof. A third bracket 58 is attached to a middle portion of the frame 46 for receiving a snap hook attached to the second end of the second adjustable seatbelt 60. As will be explained herein, another adjustable seatbelt having the same configuration and dimension may be used for securing the left leg of the user. Moreover, the second adjustable seatbelt 60, or other seatbelts, may include a Velcro-type securing means for adjusting the length of the seatbelt.

Moreover, the frame 46 is pivotally attached at a rear end thereof to a bracket 62 extending from a front face 61 of the vertical post 36. A second electric actuator arm 64 has a first end 66 attached to a lower surface of the frame 46 and a second end 68 attached to the support platform 18, wherein the second electric actuator arm 64 adjusts the height of horizontal portion 28 to a desired height by tilting the horizontal portion 28 about the pivot point where it is attached to the bracket 62.

The isokinetic testing apparatus 10 further includes a first main arm 70 having a proximal apex end 72 and a distal end 74, and a second main arm 76 having a proximal apex end 78 and a distal end 80, wherein the first and the second main arms 70, 76 extend substantially the length of the support frame 12 and are dimensioned and configured to bound the adjustable seat 24 within a space therebetween.

A gear assembly 82 is disposed and supported on a sub-assembly 84 slidably supported on and proximate to the first rail second end 13 and second rail second end 17 and within second elongate slots 21, 23. The sub-assembly 84 houses a PLC, a motor drive, an electric actuator control box, and a terminal strip therewithin for operating the isokinetic apparatus. The sub-assembly 84 horizontally slides along the first and the second rails 14, 16 by a third electric actuator arm 86 attached to the lower portion of the sub-assembly 84 at one end 88 and attached to the support platform 18 at a second end 90.

The first main arm 70 is pivotally and operably attached to the gear assembly 82 at its distal end 74, and the second main arm 76 is pivotally and operably attached to the gear assembly 82 at its distal end 80.

A fourth electric actuator arm 92 includes a first end 94 attached to a mid-section of the first main arm 70, and a second end 96. A rail 97 is positioned within the first rail elongate slot 20 and includes a first end and a second end, wherein the second end 96 of the fourth electric actuator arm 92 is attached to the first end of the rail 97, and the second end of the rail 97 is attached to a lower portion of the subassembly at 99, thereby allowing the fourth electric actuator arm 92 and the subassembly 84 to move together. The fourth electric actuator arm 92 adjusts the height of the first proximal apex end 72 of the first main arm 70 by raising the main arm 70 as it pivots about its distal end 74.

Similarly, a fifth electric actuator arm 98 includes a first end 100 attached to a mid-section of the second main arm 76, and a second end 102. A second rail 101 is positioned within the second rail elongate slot 22 and includes a first end and a second end, wherein the second end 102 of the fifth electric actuator arm 98 is attached to the first end of the second rail 101, the second end of the rail 101 is attached to a lower portion of the subassembly at 103, thereby allowing the fifth electric actuator arm 98 and the subassembly 84 move together. The fifth electric actuator arm 98 adjusts the height of the proximal apex end 78 of the second main arm 76 by raising the second main arm 76 as it pivots about its distal end 80.

Referring more specifically to FIG. 1, a torque arm 104 is pivotally and releasably attached to the first main arm proximal apex end 72 on the outside of the first main arm, wherein the torque arm 104 is tightened and released by a screw means or a clamping mechanism 106. The torque arm 104 pivots relative for the first main arm 70 about the proximal apex end 72 by a chain or belt drive mechanism operably connected to the gear assembly 82.

The chain drive mechanism includes a first sprocket gear 108 rotatably positioned and disposed within the first main arm 70 at the proximal apex end 72, and a second sprocket gear 110 rotatably positioned and disposed within the first main arm 70 at the distal end 74. A chain or belt 112 loops around and engages with the first and the second sprocket gears 108, 110, within and spanning the whole length of the first main arm 70, wherein the second sprocket gear 110 is attached and operably connected to the shaft of the gear assembly 82.

The torque arm 104 includes an arm extension 114 removably and slidably disposed within the torque arm 104 casing and secured at a desired length and position by a threaded knob 118 or other suitable securing means. The arm extension 114 further includes a handle portion 116 to be gripped by a user's hand during testing of the user's shoulder, as will be explained in greater detail herein.

It is noted that the second main arm 76 includes identical structural parts and mechanisms as the first main arm 70. As will be explained, the torque arm 104 is attached to the first main arm 70 to conduct the testing of the left shoulder and the left knee of the user, and a second torque arm 104' may be attached to the second main arm 76 in a similar manner as the torque arm 104 attached to the first main arm 70 to conduct the testing of the right shoulder and the right knee of the user. That is, the second torque arm 104' includes an arm extension 114' removably and slidably disposed within the torque arm 104' casing and secured at a desired length and position by a threaded knob 118' or other suitable securing means. The arm extension 114' further includes a handle portion 116' to be gripped by a user's hand during testing of the user's shoulder.

Furthermore, in order to conduct testing of the knees of a user, the arm extension 114 (or the arm extension 114') is replaced with a leg extension 120, as best seen in FIG. 3, slidably secured within the toque arm 104 and secured by the threaded knob 118. The leg extension 120 includes a belt strap 122 for securing the leg extension to the user's leg above the ankle.

Figure 4:
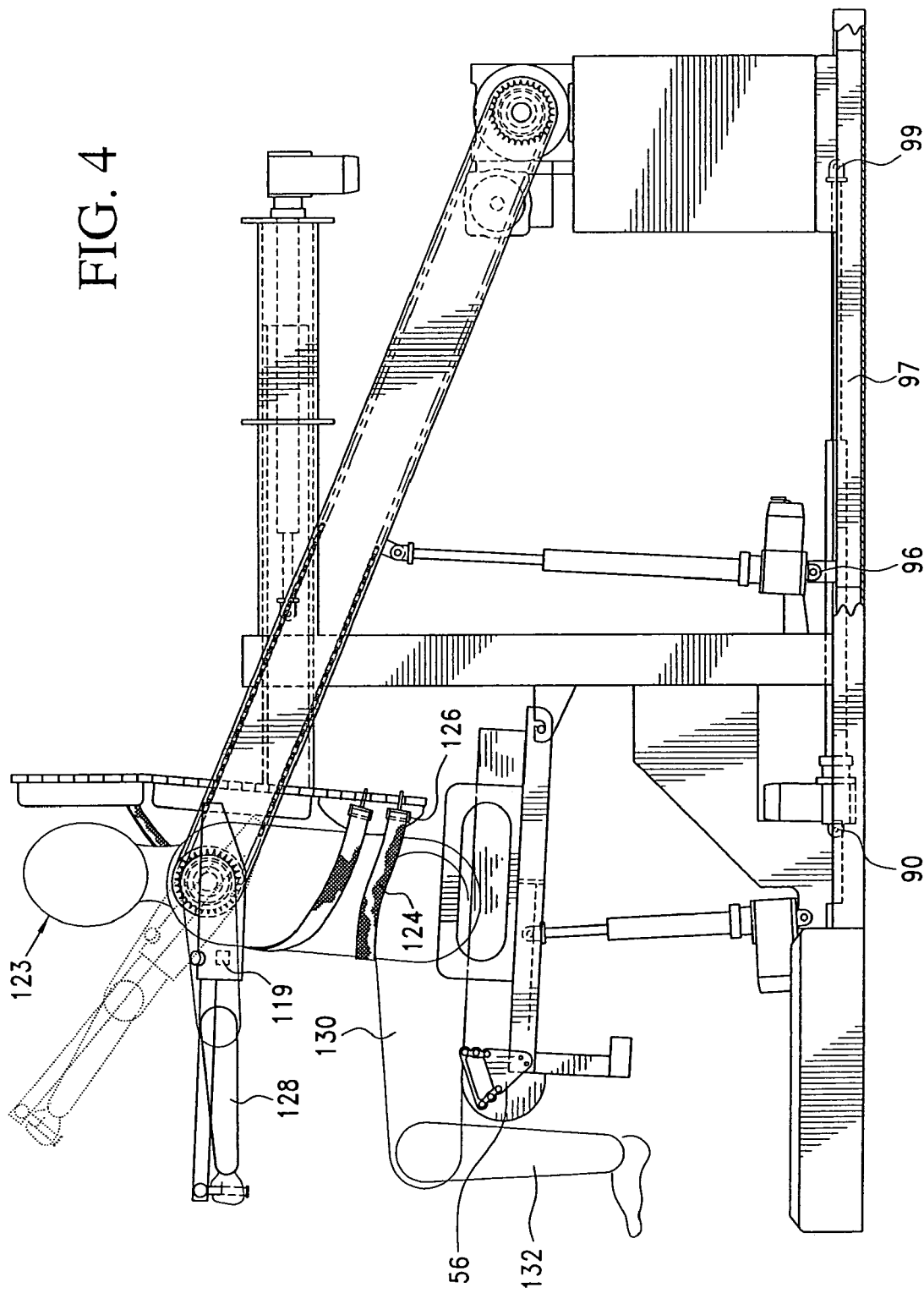
FIG. 4 is a side elevational view of the isokinetic testing apparatus according to a first representative embodiment being used by a user for the testing of the left shoulder; and, FIG. 5 is a side elevational view of the isokinetic testing apparatus according to a first representative embodiment being used by a user for the testing of the back.

Referring now to FIGS. 1 and 4, the use of the isokinetic testing apparatus for testing the left shoulder strength of the user is explained. As a preliminary matter, the user 123 is seated on the adjustable seat 24 and positioned in an optimal testing seated position by adjusting the vertical back portion 26 with the first electric actuator arm 34, adjusting the height of the horizontal portion 28 with the second electric actuator arm 64, adjusting the first main arm 70 with the fourth electric actuator arm 92, and also adjusting the main arm with the sliding movement of the sub-assembly 84 so that the apex of the arm at the shoulder coincides and aligns with the first main arm proximal apex end 72.

Next, the user 123 is strapped-in by extending the first adjustable seatbelt 44 across the user's chest and securing the seatbelt buckle 42 through the appropriate hole or aperture 38. A third seatbelt 124 is extended across the user's lower abdomen and the snap hook 126 is secured at one of the plurality of holes or apertures 38 of the main plate 30. Now, the threaded knob 118 is loosened to release the arm extension 114, wherein the arm extension is slid outwardly from the torque arm 104 to the extent that when the user's left arm 128 is straight, and the threaded knob is tightened to secure the arm extension 114 in that position. The user then grabs and holds the handle portion 116, and the testing may begin.

As the user tries to pivot the torque arm 104, the voltage readout from a load cell 119 is converted to the force (torque) output in the torque arm 104 for the left shoulder and is stored by a personal computer 130 operably connected to the isokinetic testing apparatus 10, and the reading is stored and associated with the user's profile and saved in a database in the personal computer. As will be explained in greater detail, the torque readings from the testing of the knees, the shoulders, and the back of a user are converted to an overall strength rating, which is associated with the composite strength of the user, and which can be used in determining whether that user has the strength to perform a specific job or task.

Moreover, in order to test the strength of the right shoulder of the user, the second torque arm 104' is attached to second main arm 76 on the outside thereof in the manner similar to setting up the torque arm 104 for testing the left shoulder as explained hereinabove, and the similar steps as the testing of the left shoulder is performed. It is also noted that the second torque arm 104' includes identical parts and structural configuration as the torque arm 104.

Referring now to FIG. 3, the use of the isokinetic testing apparatus for testing the left knee 132 and knee joint strength of the user is explained. As stated hereinabove, underlying the present invention is an isokinetic testing apparatus wherein the user may be seated and remain in the same position to conduct the testing of the knees without requiring the user to move to a different testing station.

Now, the arm extension 114 is removed and replaced with the leg extension 120 on the torque arm 104. It is noted that the torque arm 104 (and the second torque arm 104') is detached from the outside of the main arm and is pivotally attached to the inside of the main arm 70 for testing the right and the left knees. The user 123 is seated on the adjustable seat 24 and positioned in an optimal testing seated position by adjusting the vertical back portion 26 with the first electric actuator arm 34, adjusting the height of the horizontal portion 28 with the second electric actuator arm 64, adjusting the first main arm 70 with the fourth electric actuator arm 92, and also adjusting the main arm by sliding the sub-assembly 84 so that the apex of left knee joint coincides and aligns with the first main arm proximal apex end 72.

The user 123 is then strapped-in by extending the first adjustable seatbelt 44 across the user's chest and securing the seatbelt snap hook 42 at one of the plurality of holes or apertures 38. The second adjustable seatbelt 60 is moved across and on top of the user's left thigh and the snap hook 59 is secured to the third bracket 58. The third seatbelt 124 is extended across the user's lower abdomen and the buckle 126 is secured at one of the plurality of loops 38 of the main plate 30.

Now, the threaded knob 118 is loosened to release the leg extension 120, wherein the leg extension 120 is slid outwardly from the torque arm 104 to the extent that the belt strap 122 is right above the user's ankle and secured thereto, and the threaded knob 118 is tightened to secure the leg extension 120 in that position.

As the user tries to pivot the torque arm 104 by bending his or her left knee 132, the force (torque) output from the load cell 119 for the left knee is read and stored by the personal computer 130, and the reading is stored and associated with the user's profile saved in a database in the personal computer.

Moreover, in order to test the strength of the right knee of the user, the second torque arm 104' is attached to inside of the second main arm 76 in the manner similar as setting up the torque arm 104 for the testing the left knee as explained hereinabove, and the similar steps for the testing of the right knee is performed.

Figure 5:
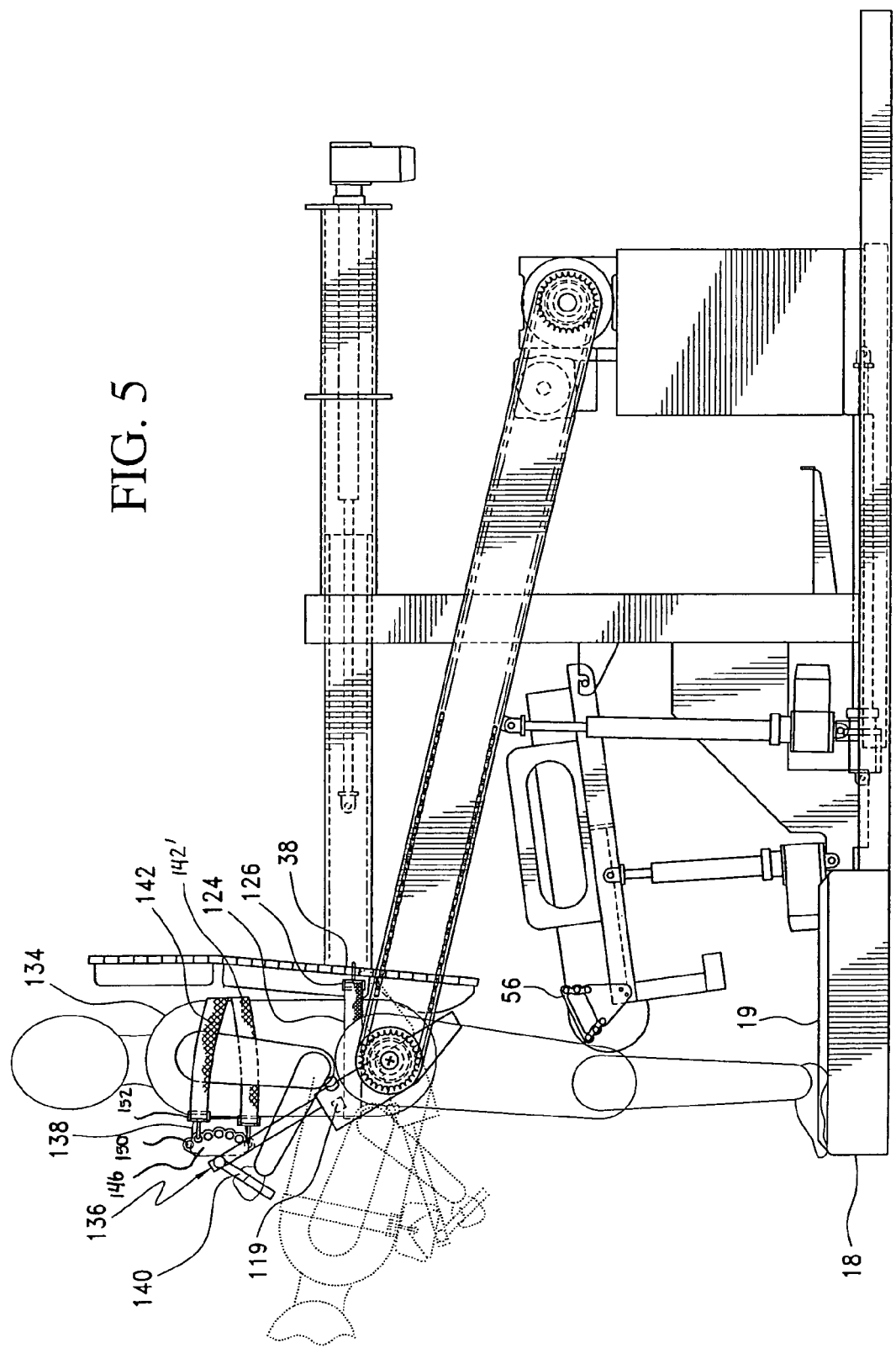

Referring now to FIG. 5, the use of the isokinetic testing apparatus for testing the back 134 of the user is explained. The testing of the back requires the use of both the torque arm 104 and the second torque arm 104' together. Again, the isokinetic testing apparatus of the present invention allows for the user to remain in substantially the same position to conduct the testing of the back without being moved to a different station.

The knee extensions 120 from the torque arm 104 and the second torque arm 104' are removed and replaced with a back extension 136 on the torque arm 104 and the second torque arm 104'. The user 123 stands up straight with both feet firmly positioned on the upper surface 19 of the support platform 18 in an optimal testing position by adjusting the vertical back portion 26 with the first electric actuator arm 34, adjusting the first main arm 70 with the fourth electric actuator arm 92, and also adjusting the first main arm 70 with the sliding movement of the sub-assembly 84 so that the apex of the user's lower waist coincides and aligns with the first main arm proximal apex end 72.

Next, the user 123 is strapped in by extending the third seatbelt 124 across the user's lower abdomen and the snap hook 126 is secured at one of the plurality of holes or apertures 38 of the main plate 30. The threaded knobs 118, 118' are loosened to release the back extension 136, wherein the back extension 136 is slid outwardly from the torque arm 104 and second torque arm 104' casing to the extent that the chest pad 138 of the back extension is positioned on the upper portion of the user's chest and secured thereto by a pair of belt straps 142, 142'. The chest pad 138 includes a pair of brackets 146 at opposing ends thereof, wherein each bracket includes a plurality of apertures 150 dimensioned and configured to receive a snap hook 152 of either belt strap 142, 142'. The threaded knobs 118, 118' are tightened to secure the back extension 136 in that position. The user then grabs the handle portions 140, and the testing may begin.

As the user tries to pivot the torque arm 104 and the second torque arm 104' by bending over and straightening up, the force (torque) output from the load cell 119, 119' for the back is read and stored by the personal computer 130, and the reading is stored and associated with the user's profile and saved in a database in the personal computer.

After the completion of the testing of the knees, the shoulders, and the back, the torque readings and the single index score of the user are stored in the user's profile, and a database is created for every single user being tested by the isokinetic testing apparatus.

Now, in order to re-test a specific user's knees, shoulders, and the back strengths in order to, for example, determine the user's strength after a rehabilitation period, it is imperative to position the first and the second main arms 70, 76, the torque arm 104 and the second torque arm 104', the arm extension 114, the leg extension 120, and the back extension 136 so that the proximal apex end of the either main arms exactly coincides and aligns with the apex of the joint the apparatus is being used to re-test the user. Otherwise, a slight offset from those apex points, for example by one inch, may result in as much as ten to twelve percent inaccurate torque readings for that joint. Therefore, during the initial testing of the user's knees, shoulders, and the back, the exact positioning of the first and the second main arms 70, 76, the torque arm 104 and the second torque arm 104', the arm extension 114, the leg extension 120, and the back extension 136 for that user are also stored and associated with the user's profile so that when the same user is re-tested, the isokinetic testing apparatus may be reconfigured to that initial exact position and configuration, thereby resulting in much more accurate re-testing of the user.

While the preferred embodiment of the invention has been shown and described, various modifications and substitutions may be made thereto without departing from the spirit and scope of the invention. Accordingly, it is to be understood that the present invention has been described by way of illustration only, and this description should not be construed as limiting to the several claims appended hereto.

What is claimed is:

1. An isokinetic testing apparatus, comprising:
a support frame;
a sub assembly disposed on said support frame;
a power means operably disposed within said sub assembly;
a first main arm having a proximal apex end and a distal end, said first main arm distal end is pivotally attached to said power means;
a first torque arm pivotally and releasably attached to said first main arm proximal apex end;
a user support area disposed on said support frame proximate to said first torque arm proximal end;
a first load cell disposed within said first torque arm for measuring the torque when said first torque arm pivots;
wherein said first main arm and said torque arm can pivot and are configured to a desired position for isokinetic testing of the knees, the shoulders, and the back of the user.

2. The isokinetic testing apparatus of claim 1, wherein said support frame further comprises a first rail, a second rail, and a user support platform attached to said first and said second rails.

3. The isokinetic testing apparatus of claim 1, further comprising a first arm extension slidably and releasably attached to said first torque arm for testing the strength of the user's right shoulder.

4. The isokinetic testing apparatus of claim 1, further comprising an adjustable seat adjustably supported on said frame.

5. The isokinetic testing apparatus of claim 1, further comprising a second main arm having a proximal apex end and a distal end, wherein said distal end is pivotally attached to said sub-assembly and operable by said power means.

6. The isokinetic testing apparatus of claim 5, wherein said user support area is disposed between said first main arm proximal apex end and second main arm proximal apex end.

7. The isokinetic testing apparatus of claim 5, further comprising a second torque arm pivotally and releasably attached to said second main arm at said proximal apex end and pivotally operable by said power means.

8. The isokinetic testing apparatus of claim 7, wherein a second load cell disposed within said second torque arm.

9. The isokinetic testing apparatus of claim 8, wherein a second arm extension slidably and releasably attached to said second torque arm for testing of the right shoulder.

10. The isokinetic testing apparatus of claim 5, further comprising a first leg extension slidably and releasably attached to said first torque arm for testing of the left knee.

11. The isokinetic testing apparatus of claim 5, further comprising a second leg extension slidably and releasably attached to said second torque arm for testing of the right knee.

12. The isokinetic testing apparatus of claim 5, further comprising a back extension slidably and releasably attached to said first and said second torque arms.

13. The isokinetic testing apparatus of claim 1, further comprising a seat having an adjustable back portion and an adjustable horizontal portion attached to said support frame.

14. The isokinetic testing apparatus of claim 13, wherein said back portion is adjustable by a first electric actuator arm.

15. The isokinetic testing apparatus of claim 13, wherein said horizontal portion is adjustable by a second electric actuator arm.

16. The isokinetic testing apparatus of claim 13, wherein said first main arm is adjustable by a third electric actuator arm.

17. The isokinetic testing apparatus of claim 13, wherein said second main arm is adjustable by a fourth electric actuator arm.

18. The isokinetic testing apparatus of claim 13, wherein the torque reading from the first load cell is stored within a database in a personal computer.

19. The isokinetic testing apparatus of claim 1, wherein the apparatus comprises at least one seatbelt for securing the user on the seat.

20. The isokinetic testing apparatus of claim 15, wherein the vertical back portion includes a plurality of apertures along a peripheral side thereof for receiving a snap lock of said seat belt.

21. The isokinetic testing apparatus of claim 20, wherein said sub-assembly is slidably disposed on said first and second rails and is slidably attached to said third electric actuator arm and said fourth electric actuator arm and are movable on said rails by a fifth electric actuator arm.

22. An isokinetic testing apparatus for testing an individual's knees, shoulders and back at a single station, said apparatus comprising:
a single testing station for the isokinetic testing of an individual's knees, shoulders and back;
means for the isokinetic testing of each of the individual's knees, shoulders and back at said single station said means comprising power means and a first main arm pivotally connected to said power means, and a torque arm operatively connected to said power means by said main arm.

23. An isokinetic testing apparatus according to claim 22 further comprising means for reporting the results of each test.

24. A method for isokinetic testing of an individual's knees, shoulders and back at a single station, said method comprising the steps of:
provided an apparatus for the isokinetic testing of an individual's knees, shoulders and back at a single station;
configuring the apparatus for isokinetic testing of the individual's knees, stabilizing the individual with respect to the apparatus and isokinetic testing of the individual's knees;
configuring the apparatus for isokinetic testing of the individual's shoulders, stabilizing the individual with respect to the apparatus and isokinetic testing of the individual's shoulders; and
configuring the apparatus for isokinetic testing of the individual's back, stabilizing the individual with respect to the apparatus for testing the back and isokinetic testing of the individual's back, and wherein the individual's knees and shoulders are tested in a seated position, and the individual's back tested in a standing position.

25. A method for isokinetic testing according to claim 24 which includes the steps of recording the results of the isokinetic testing.

26. A method for isokinetic testing according to claim 24 which includes the step of providing a power resistance and torque arm in which the testing of the knees arid shoulders involve rotation of the torque arm.

27. A method for isokinetic testing according to claim 24 further comprising the step of providing a power resistance and a first main arm pivotally connected to the power resistance and adjusting the first main arm for testing the knees, shoulders and back of an individual.

* * * * *